(12) United States Patent
Pimentel et al.

(10) Patent No.: US 8,883,470 B2
(45) Date of Patent: Nov. 11, 2014

(54) FERMENTATION OF CARBOHYDRATE

(75) Inventors: Julio Pimentel, Burford, GA (US); James D. Wilson, Milton, FL (US)

(73) Assignee: Anitox Corporation, Lawrenceville, GA (US)

(*) Notice: Subject to any disclaimer, the term of this patent is extended or adjusted under 35 U.S.C. 154(b) by 0 days.

(21) Appl. No.: 13/388,664

(22) PCT Filed: Nov. 23, 2010

(86) PCT No.: PCT/US2010/057875
§ 371 (c)(1), (2), (4) Date: Feb. 2, 2012

(87) PCT Pub. No.: WO2011/066318
PCT Pub. Date: Jun. 3, 2011

(65) Prior Publication Data
US 2012/0225465 A1 Sep. 6, 2012

Related U.S. Application Data

(60) Provisional application No. 61/264,596, filed on Nov. 25, 2009.

(51) Int. Cl.
*C12P 7/10* (2006.01)

(52) U.S. Cl.
CPC .. *C12P 7/10* (2013.01); *Y02E 50/16* (2013.01); *Y02E 50/17* (2013.01)
USPC ............. 435/165; 435/41; 435/161; 435/243; 435/255.1

(58) Field of Classification Search
None
See application file for complete search history.

(56) References Cited

U.S. PATENT DOCUMENTS

| | | | | |
|---|---|---|---|---|
| 1,723,271 | A | * | 8/1929 | Ellis .................................. 8/580 |
| 5,505,976 | A | * | 4/1996 | Bland et al. .................... 426/532 |
| 6,908,995 | B2 | | 6/2005 | Blount |
| 2006/0263484 | A1 | * | 11/2006 | Maye ............................... 426/35 |
| 2007/0292919 | A1 | | 12/2007 | Holt et al. |
| 2009/0117129 | A1 | | 5/2009 | Nash et al. |
| 2010/0297719 | A1 | * | 11/2010 | de Sa et al. .................... 435/161 |

FOREIGN PATENT DOCUMENTS

| | | |
|---|---|---|
| WO | WO 2007/145858 | 12/2007 |
| WO | WO 2008-073186 | 6/2008 |
| WO | WO 2009/001205 | 12/2008 |
| WO | WO 2009/001205 | 1/2009 |
| WO | WO 2009/001836 | 1/2009 |

OTHER PUBLICATIONS

Hynes et al., J. Ind. Microbiol. Biotechnol, 18(4):284-91 (1997).*
Gobbetti, Trends Food Sci. Technol., 9: 267-274 (1998).*
Kasier et al., J. Sci. Food Agric., 32:637-646 (1981).*
Taherzadeh et al., Chem. Eng. Sci., vol. 52, No. 15, 2653-2659 (1997).*
Oliva-Neto et al (Braz. J. Microbiol., 32:10-14 (2001).*
WO 2009/001205 International Search Report, Jan. 22, 2009, PCT.
Oct. 18, 1992, Himejima, et al., Antimicrobial terpens from oleoresin of ponderosa pine tree *Pinus ponderosa*: A defense mechanism against microbial invasion, abstract from *J Chem Ecol*, 1992, 10,1809-18, lines 6 to 11 of p. 10.
WO-2009/001205 International Search Report, Dec. 31, 2008, PCT.
WO 2009/001836 International Search Report, Jan. 22, 2009, PCT.
Aug. 30, 2011, International Search Report for PCT/US2010/057875.
Jun. 13, 2006, Spilatro et al., "Yeast on the rise: Investigative study of fermentation in the introductory biology curriculum", http://www.cur.org/rl2000/pdf/ystferm.pdf (Jun. 13, 2006).
Written Opinion of the International Search Authority for PCT/US2010/057875.
European Search Report for EP 10833878.1 dated Aug. 26, 2013.
1997, Taherzadeh etal., "Acetic acid—friend or foe in anaerobic batch conversion of glucose to ethanol by *Saccharomyces cerevisiae*?" Chemical Engineering Science, vol. 52, No. 15, pp. 2653-2659, 1997.
Jan. 1, 2005, LaLonde, R.T. 2005. Terpens and Terpenoids. Van Nostrand's Encyclopedia of Chemistry, Abstract, (hyperlink:http://onlinelibrary.wiley.com/doi/10.1002/0471740039.vec2473/abstract).
Oct. 18, 1992, Himejima, et al., Antimicrobial terpens from oleoresin of ponderosa pine tree*Pinus ponderosa*: A defense mechanism against microbial invasion, abstract from *J Chem Ecol*, 1992, 10,1809-18, lines 6 to 11 of p. 10.
2003, Bayrock, D.P., K.C.Thomas and W.M. Ingledew, 2003. Control of *Lactobacillus* contaminants in continuous fuel ethanol fermentations by constant or pulsed addition of penicillin. G. App. Microbiol. Biotechnol 62: 498-502.
2001, Bayrock, D. and W.M. Ingledew, 2001. Changes in steady state on introduction of a *Lactobacillus* contaminant to a continuous culture ethanol fermentation. J. Industrial Microbiology and Biotechnology 27: 39-45.
2009, Bischoff, K.M., S. Liu, T.D. Leathers and R.E. Worthington, 2009. Modeling bacterial Contamination of Fuel Ethanol Fermentation. Biotechno. Bioeng 103: 117-122.
2007, Bischoff, K.M., K.A. Skinner-Nemec and T.D. Leathers, 2007. Antimicrobial susceptibility of *Lactobacillus* species isolated from commercial ethanol plants. J. Ind. Microbiol. Biotechnol.

(Continued)

*Primary Examiner* — Blaine Lankford
*Assistant Examiner* — Thomas J Visone
(74) *Attorney, Agent, or Firm* — Neifeld IP Law, PC

(57) ABSTRACT

A high yield method for fermenting carbohydrate to ethanol, comprising a) treating carbohydrate with a composition containing 10-90 wt % of an aldehyde selected from the group consisting of an formaldehyde, para-formaldehyde, glutaraldehyde and mixtures thereof, 1-50 wt % of a surfactant having an I JLB from 4 to 18, 0-20 wt % of an antimicrobial terpene, or essential oils, 1-50 wt % of organic acids selected from $C_{1-24}$ fatty acids, their salts, and glyceride esters thereof, and 1-50 wt % water, b) fermenting said carbohydrate in the presence of yeast in a fermentation broth, and c) isolating ethanol in a higher yield than would be obtained without step a).

9 Claims, No Drawings

(56) References Cited

OTHER PUBLICATIONS

1997, Chang I.N., B.H. Kim and P.K. Shin, 1997. Use of sulfite and hydrogen peroxide to control bacterial contamination in ethanol fermentation. Applied and Environmental Microbiology 63(1): 1-6.

2003, Dien, B.S., M.A. Cotta and T.W. Jeffries, 2003. Bacteria engineered for fuel ethanol production: current status. Appl. Microbiol. Biotechnol. 63: 258-266.

1997, Hynes, S.H., Kjarsgaard, K.C. Thomas and W.M. Ingledew, 1 97. Use of virginiamycin to control the growth of lactic acid bacteria during alcohol fermentation. J Industrial Microbiology and Biotechnology 18: 284-291.

2006, Majovic, L, S. Nikolic, M. Rakin and M. Vukasinovic, 2006. Production of Bioethanol from Corn Meal Hydrolyzates. Fuel 85: 1750-1755.

2004, Narendranath, N. V. and R. Power, 2004. Effect of yeast inoculation rate on the metabolism of contaminant *Lactobacilli* during fermentation of corn mash. J. Ind. Microbiol. Biotechnol. 31 : 581-584.

2000, Narendranath, N.V., K.C. Thomas and W.M. Ingledew, 2000. Urea hydrogen peroxide reduces the number of *Lactobacilli*, nourish yeast, leaves no residues in the ethanol fermentation. Applied and Environmental Microbiology 66(10): 4187-4192.

2004, OlivaNeto, P., M.A. Ferreira and F. Yokoya, 2004. Screening for yeast with antibacterial properties from ethanol distillery. Bioresource Technology 92: 1-6.

2007, Skinner-Nemec, K.A., N. N Nichols and T.D. Leathers, 2007. Biofilm formation by bacterial contaminants of fuel ethanol production. Biotechnol. Lett. 29: 379-383.

2004, Skinner, K.A. and T.D. Leathers, 2004. Bacterial Contaminants of Fuel Ethanol Production. J. Ind. Microbiol. Biotech. 31: 401-408.

2001 Thomas, K.C., S.H. Hynes and W.M. Ingledew, 2001. Effect of *Lactobacilli* on yeast growth, viability and batch and semi-continuous alcoholic fermentation on corn mash. J. Applied Microbiology 90: 819-828.

\* cited by examiner

FERMENTATION OF CARBOHYDRATE

CROSS REFERENCE TO RELATED APPLICATIONS

This application is a national stage entry of PCT/US2010/057875, filed Nov. 23, 2010, which claims priority to provisional application 61/264,596, filed Nov. 25, 2009, entitled "FERMENTATION OF CARBOHYDRATE" incorporated herein by reference.

BACKGROUND OF THE INVENTION

1. Field of the Invention

A high yield method for producing ethanol from carbohydrate fermentation, by treating incoming carbohydrate material with an aldehyde, a fatty acid, a terpene and a surfactant.

2. Background

In 2009, the Renewable Fuels Standard (RES) called for blending 11.1 billion gallons of ethanol and other biofuels into the U.S. motor fuels market to satisfied future demands. This will result in an increase in the level of corn needed by the industry and require plant capacity to be increased as well. In just the past year, the USA's annual operating capacity increased by 2.7 billion gallons, a 34% increase over 2007. This growth in production capacity was enabled by the completion, start-up, and operation of new ethanol refineries.

Ethanol, a promising biofuel from renewable resources, is produced from the starch of cereal grains (corn, sorghum, wheat, triticale, rye, malted barley, rice), tuber crops (potatoes) or by direct use of the sugar in molasses, sugar cane juice or sugar beet juice. Ethanol can also be produced by fermentation of cellulose-based material (switch grass, pine trees), but this technology has not been widely commercialized.

Eighty percent of the world ethanol is produced by Brazil and the USA. Of this, 60% is produced by yeast fermentation of corn or sugar cane juice. Ethanol production through anaerobic fermentation of a carbon source by the yeast *Saccharomyces cerevisiae* is one of the best known biotechnological processes and accounts for a world production of more than 35 billion liters of ethanol per year (Bayrock, 2007).

The process of ethanol production from cereals begins with the hydrolysis of starch. The hydrolysis of starch results in the conversion of amylose, a mostly linear α-D-(1-4)-glucan, and branched amylopectin, a α-D-(1-4)-glucan which has α-D-(1-6) linkages at the branch point, into fermentable sugars that subsequently are converted to ethanol by yeast (Majovic, 2006), bacteria (Dien, 2003). Bacteria are used for the production of ethanol from mostly cellulose containing material, they include *Zymomonas* spp., engineered *E. coli, Klebsiella oxytoca, Zymomonas mobilis, Acetivibrio celluloyticus* within others (Dien, 2003)

In an ethanol production system, whole corn kernel is ground and mixed with water. The mixture is then steam cooked to gelatinize starch and to decrease bacterial contamination. After this liquefaction, enzymes and yeast are added to start the fermentation process to produce ethanol.

Dry milling and wet milling are the two primary processes used to make ethanol in the United States.

In the dry milling process, the entire corn kernel or other starchy material is ground into flour and mixed with water to form a slurry. Then, enzymes are added to the mixture, which is processed in a high-temperature cooker, cooled and transferred to fermenters where yeast is added and the conversion of sugar to ethanol begins. After fermentation, the resulting mixture is transferred to distillation columns where the ethanol is separated. The solids resulting after fermentation and ethanol separation are processed to produce distiller's dried grains with solubles (DDGS) which is used for animal production, e.g. poultry, swine, and cattle feed. More than 80% of today's ethanol capacity utilizes the dry mill process (RFS, 2006).

In the wet milling process, the grain is soaked or steeped in water to facilitate the separation of the grain into its basic nutritional components, such as corn germ, fiber, gluten and starch components. After steeping, the corn slurry is processed through a series of grinders and the components separated. The gluten component is filtered and dried to produce the corn gluten meal (CGM), a high-protein product used as a feed ingredient in animal operations. The starch and any remaining water from the mash are then processed in one of three ways: Fermented into ethanol, dried and sold as dried or modified corn starch, or processed into corn syrup (RFS, 2006).

Both the wet and dry mill processes utilize only the starch portion of the corn kernel for ethanol production. The remaining protein, fat, fiber and other nutritional components remain available for use as animal feed.

In the conventional fermentation process, yeast culture is added to the starch kernel portion of the corn and incubated 72 hours to allow sufficient time for the yeast population to increase to the necessary concentration (Maye, 2006). It takes from 45 to 60 minutes for the yeast population to double. It takes many hours of such propagation to produce the quantity of yeast necessary to ferment such a large quantity of sugar solution (Maye, 2006).

A process called raw starch hydrolysis converts starch to sugar which is then fermented to ethanol, bypassing conventional starch gelatinization conditions. The enzymes used in the saccharification/fermentation are fungal alpha amylase and glucoamylase (amyloglucosidase) (Thomas, 2001). This simultaneous saccharification and fermentation allows for higher concentrations of starch to be fermented and results in higher levels of ethanol. If the sugar source is from crops such as sugar cane, sugar beets, fruit or molasses, saccharification is not necessary and fermentation can begin with the addition of yeast and water (Maye, 2006).

One of the important concerns with batch or continuous fermentation systems is the difficulty of maintaining it free from bacterial contamination. Unfortunately, the optimum atmosphere for fermentation is also optimum for bacterial growth. Contamination generally originates from harvesting of the carbohydrate material. Washing the material may help lower the contamination level (Maye, 2006).

Despite efforts to prevent contamination with cleaning and disinfecting of the saccharification tanks and continuous yeast propagation systems, biofilms can act as reservoirs of bacteria that continuously reintroduce contaminants (Bischoff, 2009).

A variety of gram positive and gram negative bacteria have been isolated from fuel ethanol fermentation including species of *Lactobacillus, Pediococcus, Staphylococcus, Enterococcus, Acetobacter, Gluconobacter* and *Clostridium* (Bischoff, 2009). Almost two thirds of the bacteria isolated were species of lactic acid bacteria, e.g. *Lactobacillus* (Skinner, 2007).

In a survey conducted by Skinner and Leathers (2004), 44-60% of the contaminants in the wet mill process were identified as Lactobacilli. In the dry mill process, 37 to 87% of the contaminants were identified as Lactobacilli.

Lactobacilli contamination in the range of $10^6$ to $10^7$ cfu/mL corn slurry can reduce ethanol yield by 1-3%. In industry, even with an active bacterial control program to control the proliferation of Lactobacilli, carbohydrate losses to Lactobacilli can make the difference between profitability and non-profitability (Bayrock, 2007). Lactobacilli not only tolerate low pH, high acidity and relatively high concentrations of ethanol, but they also multiply under conditions of alcoholic fermentation (Thomas, 2001). Bacterial contaminants compete for growth factors needed by yeast and also produce by-products that are inhibitory to yeast, particularly lactic and acetic acids.

The contamination of carbohydrate slurry during the course of alcoholic fermentation results in a) decreased ethanol yield, b) increased channeling of carbohydrates for the production of glycerol and lactic acids, c) a rapid loss of the yeast viability after exhaustion of fermentable sugars, and d) decreased proliferation of yeast in the mash in which the contaminating Lactobacilli has already grown to a high number (Thomas, 2001).

A recent survey of bacterial contaminants of corn-based plants in the US found that bacterial loads in a wet mill facility were approximately $10^6$ cfu/mL corn slurry while those at dry-grind facilities could reach $10^8$ cfu/mL corn slurry (Bischoff, 2007; Chang, 1997).

The presence of *Lactobacillus* byproducts, i.e. acetic and lactic acids, during fermentation affects yeast growth and metabolism, and it has been suggested as one of the causes of stuck, or sluggish fermentation (Thomas, 2001). If the lactic acid content of the mash approaches 0.8% and/or acetic acid concentration exceeds 0.05%, the ethanol producing yeast are stressed (Bayrock, 2007). Lactobacilli may stress yeast cells, which release nutrients, particularly amino acids and peptides that can stimulate bacterial growth (Oliva-Neto, 2004). A lactic acid concentration of 8 g/L in a beet molasses batch fermentation reduced yeast viability by 95% and alcohol production rate by 80% (Bayrock, 2001).

The presence of *Lactobacillus* in the ethanol fermentation can decrease ethanol yield by 44% after 4 days of pH1 controlled operation. This coincides with an increase in *L. paracasei* to >$10^{10}$ cfu/mL and a fourfold increase in lactic acid concentration to 20 g/L. An 80% reduction in yeast density was seen with concentrations of ethanol, lactic acid and acetic acid of 70, 38 and 7.5 g/L respectively (Bayrock, 2001).

De Oliva-Neto and Yokoya (1994) evaluated the effect of bacterial contamination on a batch-fed alcoholic fermentation process. They showed that *L. fermentum* will strongly inhibit commercial baker's yeast in a batch-fed process. When the total acid (lactic and acetic) exceeded 4.8 g/L it interfered with yeast bud formation and viability with 6 g/L decrease in alcoholic efficiency.

Others have shown that: a) a $10^6$ Lactobacilli/mL mash results in approx 1% v/v reduction in the final ethanol produced by yeast (Narendranath, 2004), b) challenging the fermentation system with $10^8$ cfu/mL *L. fermentum* decreased ethanol yield by 27% and increased residual glucose from 6.2 to 45.5 g/L (Bischoff, 2009), c) the use of $10^3$ cfu Lactobacilli/mL produced an 8% reduction in ethanol yield and a 3.2 fold increase in residual glucose (Bischoff 2009).

Methods to control bacteria include the addition of more yeast culture, stringent cleaning and sanitation, acid washing of yeast destined for reuse, and the use of antibiotics during fermentation (Hynes, 1997). An increased yeast inoculation rate of $3 \times 10^7$ cfu/mL. mash resulted in greater than 80% decrease in lactic acid production by *L. plantarum* and greater than 55% decrease in lactic acid production by *L. paracasei*, when mash was infected with $1 \times 10^8$ Lactobacilli/mL (Narendranath, 2004; Bischoff, 2009).

Various agents have been tested for control of bacterial contaminants in laboratory conditions including antiseptics such as hydrogen peroxide, potassium metabisulfite, and 3,4, 4'-trichlorocarbanilide and antibiotics such as penicillin, tetracycline, monensin and virginiamycin. Penicillin and virginiamycin are commercially sold today to treat bacterial infections of fuel ethanol fermentation and some facilities use these antibiotics prophylactically (Skinner, 2004).

If no antibiotics are used, a 1 to 5% loss in ethanol yield is common. A fifty million-gallon fuel ethanol plant operating with a lactic acid level of 0.3% w/w in its distiller's beer is losing approximately 570,000 gallons of ethanol every year due to bacterial contamination (Maye, 2006). In the absence of an antibiotic, bacterial numbers increased from $1 \times 10^6$ cfu/mL to $6 \times 10^6$ cfu/mL during a 48 hour fermentation period and 5.8 mg lactic acid was produced (Hynes, 1.997).

One very effective bacterial control program involves the use of virginiamycin. Some characteristics of virginiamycin are a) at low concentrations, e.g., 0.3 to 5 ppm it is effective against a number of microorganisms including Lactobacilli, b) the microorganisms do not tend to develop resistance, c) it does not significantly inhibit the yeast, d) it is not affected by the pH or alcohol concentration, and e) it is inactivated during ethanol distillation, therefore no residue remains in the alcohol or distilled grains (Bayrock, 2007; Narendranath 2000; Hynes, 1997).

Currently, virginiamycin is the only antibiotic known to be used at the dry-grind plant (Bischoff, 2007). The recommended dose of virginiamycin in fuel ethanol fermentations is generally 0.25 to 2.0 ppm (Bischoff, 2009) but the Minimum Inhibitory Concentration (MIC) varies from 0.5 to greater than 64 ppm (Hynes, 1997).

*L. fermentum* could be selectively controlled by hydrogen peroxide at concentrations of 1 to 10 mM in an ethanol fermentation process (Narendranath, 2000). *Lactobacillus* does not have the enzyme catalase, so it cannot decompose hydrogen peroxide and therefore is unable to eliminate its toxic effect (Narendranath, 2000).

Urea hydrogen peroxide (UHP) has been used as an antiseptic for topical applications on wounds and against gingivitis and dental plaque (Narendranath, 2000) and also serves as an antibacterial during fermentation UHP not only exhibits excellent bactericidal activity against *Lactobacillus* but also has an important advantage of providing usable nitrogen in the form of urea for stimulating yeast growth and fermentation rates (Narendranath, 2000).

Other methods of controlling bacterial contamination include the use of sulfites. Sulfites demonstrate bactericidal activity only in the presence of oxygen and were more effective in killing facultative *L. casei* which possess high levels of hydrogen peroxide related enzymes, including peroxidase (Chang, 1997) Bacterial load was also decreased when the concentration of sulfite ranged from 100 to 400 mg/L but only in the presence of oxygen. This concentration did not affect yeast populations (Chang, 1997).

An agent present in the supernatant of yeast cultures reduces the growth of Lactobacilli. This compound has not yet been characterized, though it is known to be resistant to freezing, unstable at high temperatures and destroyed when held at 90° C. for 20 minutes (Oliva-Neto 2004).

Succinic acid by itself at levels of 600 mg/L reduces *Lactobacillus* concentrations by 78%, in the presence of ethanol that reduction is up to 96% (Oliva-Neto 2004).

A microbial adherence inhibitor in the form of fowl egg antibodies and specific to lactic acid-producing microorganisms has been developed for use in fermenters (Nash 2009).

Only laboratory studies have shown that antibodies, sulfite and peroxide products can be beneficial in controlling lactobacilli, a problem with these products is the decrease in concentration due to oxidation and decomposition of the chemicals which will require constant monitoring of the whole process of fermentation in order to maintain an effective concentration. Decreased susceptibility to virginiamycin has been observed in *Lactobacilli* isolated from dry-grind ethanol plants that use virginiamycin and the emergence of isolates with multi-drug resistance to both penicillin and virginiamycin has also been reported (Bischoff 2009). So alternatives to prevent decreased ethanol yield from carbohydrate fermentation are needed.

REFERENCES

Bayrock, Dennis, 2007. Method of reducing the growth of *lactobacillus* in a process of ethanol production by yeast fermentation comprising adding a pristinamycin type antimicrobial agent and/or a polyether ionophore antimicrobial agent dissolved in an organic solvent. PCT patent #WO 2007/145858

Bayrock, D. P., K. C. Thomas and W. M. Ingledew, 2003. Control of *Lactobacillus* contaminants in continuous fuel ethanol fermentations by constant or pulsed addition of penicillin. G. App. Microbiol. Biotechnol 62: 498-502.

Bayrock, D. and W. M. Ingledew, 2001. Changes in steady state on introduction of a *lactobacillus* contaminant to a continuous culture ethanol fermentation. J. Industrial Microbiology and Biotechnology 27: 39-45.

Bischoff, K. M., S. Liu, T. D. Leathers and R. E. Worthington, 2009. Modeling bacterial Contamination of Fuel Ethanol Fermentation. Biotechno. Bioeng. 103: 117-122.

Bischoff, K. M., K A Skinner-Nemec and T. D. Leathers, 2007. Antimicrobial susceptibility of *Lactobacillus* species isolated from commercial ethanol plants. J. Ind. Microbiol. Biotechnol.

Chang I. N., B. H. Kim and P. K. Shin, 1997. Use of sulfite and hydrogen peroxide to control bacterial contamination in ethanol fermentation. Applied and Environmental Microbiology 63(1) 1-6.

Dien, B. S., M. A. Cotta and T. W. Jefries, 2003. Bacteria engineered for fuel ethanol production: current status. Appl. Microbiol. Biotechnol, 63: 258-266.

Hynes, S. H., Kjarsgaard, K. C. Thomas and W. M. Ingledew, 1997. Use of virginiamycin to control the growth of lactic acid bacteria during alcohol fermentation. J Industrial Microbiology and Biotechnology 18: 284-291.

Majovic, L, S. Nikolic, M. Rakin and M. Vukasinovic, 2006. Production of Bioethanol from Corn Meal Hydrolyzates, Fuel 85: 1750-1.755.

Maye, John P., 2006. Use of hop acids in fuel ethanol production. US patent application #20060263484

Narendranath, N. V. and R. Power, 2004, Effect of yeast inoculation rate on the metabolism of contaminant lactobacilli during fermentation of corn mash. J. Ind. Microbiol. Biotechnol. 31: 581-584.

Narendranath, N. V., K. C. Thomas and W. M. Ingledew, 2000. Urea hydrogen peroxide reduces the number of lactobacilli, nourish yeast, leaves no residues in the ethanol fermentation. Applied and Environmental Microbiology 66(10): 4187-4192.

Nash, Peter, et al 2009. Immunogen adherence inhibitor directed to *lactobacillus* organisms and method of making and using it. United States Patent Application #20090117129

Oliva Neto, P., M. A. Ferreira and F. Yokoya, 2004. Screening for yeast with antibacterial properties from ethanol distillery. Bioresource Technology 92: 1-6.

RFA "Renewable Fuels Association 2006 and 2009.

Skinner-Nemec, K. A., N. N. Nichols and T. D. Leathers, 2007. Biofilm formation by bacterial contaminants of fuel ethanol production. Biotechnol. Lett. 29: 379-383.

Skinner, K. A and T. D. Leathers, 2004. Bacterial Contaminants of Fuel Ethanol Production. J. Ind. Microbiol. Biotech. 31: 401-408.

Thomas, K. C., S. H. Hynes and W. M. Ingledew, 2001. Effect of lactobacilli on yeast growth, viability and batch and semi-continuous alcoholic fermentation on corn mash. J. Applied Microbiology 90: 819-828.

SUMMARY OF THE INVENTION

An object of the invention is to provide a chemical composition that prevents "stuck fermentation" during ethanol production by inhibiting or reducing the growth of *Lactobacillus* spp. and other bacteria during fermentation of corn, other starch or cellulose based material.

Another object is to provide a method of fermenting carbohydrates to ethanol, comprising:
a) treating carbohydrate to be fermented with a composition containing
10-90 wt. % of an aldehyde selected from the group consisting of formaldehyde, paraformaldehyde, glutaraldehyde and mixtures thereof,
1-50 wt. % of a surfactant having an HLB from 4 to 1.8.
0-20 wt. % of an antimicrobial terpene, or essential oils,
1-50 wt. % of organic acids selected from $C_1$ to $C_{24}$ fatty acids, their salts, glycerides and esters thereof and
1-50 wt. % water;
b) fermenting said carbohydrate in the presence of yeast and/or an enzyme in the fermentation broth, and
c) isolating ethanol.

Another object of the invention is to provide a method of increasing ethanol production in an initially stuck fermentation system by adding a composition comprising:
a) 10-90 wt. % of an aldehyde selected from the group consisting of formaldehyde, para-formaldehyde, glutaraldehyde and mixtures thereof,
b) 1-50 wt. % of a surfactant having an HLB from 4 to 18,
c) 1-20 wt. % of an antimicrobial terpene, or essential oils,
d) 1-50 wt. % of organic acids selected from $C_1$ to $C_{24}$ fatty acids, their salts, glycerides and esters thereof, and
e) 1-50 wt. % water.

Another object of the invention is to reduce the use of antibiotics during the fermentation of carbohydrates adding to the fermentation system a composition comprising:
a) 10-90 wt. % of an aldehyde selected from the group consisting of formaldehyde, para-formaldehyde, glutaraldehyde and mixtures thereof,
b) 1-50 wt. % of a surfactant having an HLB from 4 to 18
c) 1-20 wt. % of an antimicrobial terpene, or essential oils,
d) 1-50 wt. % of organic acids selected from $C_1$ to $C_{24}$ fatty acids, their salts, glycerides and esters thereof, and
e) 1-50 wt. % water.

Another object of the invention is to reduce the antibiotic presence in the resulting sub-product of carbohydrates fermentation e.g. distilled grains, corn gluten and others.

Another object of the invention is to reduce antibiotic residues in animal products by feeding the animals sub-products of fermentation resulting from non-antibiotics but the present invention treated substrates.

Another object is to inhibit the development of antibiotic-resistant strains of bacteria which occur during fermentation.

Another object is to increase the yield of ethanol from fermented carbohydrate.

DESCRIPTION OF THE PREFERRED EMBODIMENTS

Definitions

"Stuck Fermentation" occurs when fermentation of starch to ethanol is incomplete and has stopped due to high bacterial concentration and acid content in the fermenter.

"Weight percent" (wt. %) of a component is based on the total weight of the formulation or composition in which the component is included.

"Aldehyde" includes formaldehyde, paraformaldehyde, and other active aldehydes.

"Organic acid" includes formic, acetic, propionic, butyric and other $C_1$ to $C_{24}$ fatty acids, or mono-, di-, or triglycerides of $C_1$ to $C_{24}$ organic fatty acids or their esters.

"Antimicrobial terpene" can include allyl disulfide, citral, pinene, nerol, geraniol, carvacrol, eugenol, carvone, anethole, camphor, menthol, limonene, farnesol, carotene, thymol, borneol, myrcene, terpenene, linalool, or mixtures thereof. More specifically, the terpenes may comprise allyl disulfide, thymol, citral, eugenol, limoene, carvacrol, and carvone, or mixtures thereof. The terpene component may include other terpenes with anti-microbial properties and essential oils.

Bacteria that may interfere with ethanol fermentation include *Lactobacillus* and *Leuconostoc*, which cause the most problems. Other such bacteria include *Pediococcus, Staphylococcus, Streptococcus, Bacillus* and *Clostridia*.

In ethanol produced from corn, antibiotics are the common biocide, e.g., virginimicin, penicillin, clindamycin, tylosin, chloramphenicol, cephalosporin and tetracycline.

However in ethanol produced from sugarcane, since the end product is not fed to animals, other biocides can be used since residues do not present the same problem. In such cases suitable biocides include carbamates, quaternary ammonium compounds, phenols and antibiotics (e.g., virginiamycin, penicillin, clindamycin, tylosin, chloramphenicol, cephalosporin and tetracycline).

The term "effective amount" of a compound means an amount capable of performing the function or having the property for which the effective amount is expressed, such as a non-toxic but sufficient amount to provide anti-microbial benefits. Thus an effective amount may be determined by one of ordinary skill in the art by routine experimentation.

Formulations vary not only in the concentrations of the major components, e.g., aldehydes, the organic acids, but also in the type of terpenes, surfactant(s) and water concentration. This invention can be modified by adding or deleting the terpene, type of organic acid, and using other type of surfactant.

Composition(s)

In general, a composition of the invention contains:
a) 10-90 wt. % of an aldehyde selected from the group consisting of formaldehyde, para-formaldehyde, glutaraldehyde and mixtures thereof,
b) 1-50 wt. % of a surfactant having an HLB from 4 to 18,
c) 1-20 wt. % of an antimicrobial terpene, or essential oils,
d) 1-50 wt. % of an organic acid or mixtures of organic acids selected from acetic, propionic, butyric, or other $C_1$ to $C_{24}$ fatty acids, salt forms, glycerides and esters thereof and,
e) 1-50 wt. % water.

The antimicrobial terpenes, plant extracts or essential oils containing terpenes can be used in the compositions of this invention as well as the more purified terpenes. Terpenes are readily available commercially or can be produced by methods known in the art, such as solvent extraction or steam extraction/distillation or chemical synthesis.

The surfactant is non-ionic including ethoxylated castor oil surfactants with 1 to 200 ethylene molecules distributed normally around the mean, preferably a mean of 10 to 80. Other surfactants with similar characteristics can be used including Tween surfactants.

Methods

The present invention is effective against bacteria. Examples of these infective agents include *Lactobacillus* spp., *E. coli, Salmonella* spp., *Clostridium* spp., *Campylobacter* sp., *Shigella* spp., *Brachyspira* sp., *Listeria* spp., *Arcobacter* spp., and others.

The mixture of the present invention is applied by a spray nozzle.

The mixture is applied so as to provide a uniform and homogeneous distribution throughout the carbohydrate substrate.

Various patents and publications are referenced throughout this specification. The disclosures of each document are hereby incorporated by reference in their entirety.

EXAMPLES

Example 1

This example shows the formulation of the formaldehyde-based product used in subsequent examples

| Formula A | |
|---|---|
| Ingredient | (%) |
| Formalin (37%) | 90.00 |
| Propionic Acid | 9.00 |
| d-Limonene (terpene) | 0.35 |
| T-Maz 80 (surfactant) | 0.65 |

Example 2

The objective of this study was to determine the effect of a Formula A on the survival of *Lactobacillus*.

Material and Methods:

*Lactobacillus plantarum* (B-4496) was obtained from USDA-Microbial Genomics and Bioprocessing Research in Illinois. *L. plantarum* was grown in Difco™ Lactobacilli MRS (Man-Rogosa-Sharpe) broth. The broth culture was diluted with sterile peptone water to obtain different concentrations of *Lactobacillus*. Dilutions were treated with different concentrations of Formula A (0, 1, 2 and 3 kg/MT) and incubated for 24 hours at room temperature (20° C.). After incubation, triplicate samples were taken and plated on MRS broth containing 1.5% Difco™ Agar Granulated solidifying agent. Plates were incubated at 37° C. overnight and colonies enumerated after 24 hours. The average cfu/mL for each treatment is shown in the following table:

| Treatment | Lactobacillus (cfu/mL) | | | | | | |
|---|---|---|---|---|---|---|---|
| Control (0 kg/MT) | $4.1 \times 10^7$ | $4.8 \times 10^6$ | $5.2 \times 10^5$ | $4.8 \times 10^4$ | $3.3 \times 10^2$ | $5.3 \times 10^1$ | $4.0 \times 10^9$ |
| Formula A - 1 kg/MT | $5.0 \times 10^7$ | $1.2 \times 10^6$ | $8.6 \times 10^5$ | $7.9 \times 10^3$ | 0 | 0 | 0 |
| Formula A - 2 kg/MT | 0 | 0 | 0 | 0 | 0 | 0 | 0 |
| Formula A - 3 kg/MT | 0 | 0 | 0 | 0 | 0 | 0 | 0 |

It was observed that the use 2 kg/MT of the formaldehyde-based product reduced the growth of Lactobacillus in a culture containing $10^7$ cfu/ml.

Example 3

The objective of this study was to determine the effect of Formula A on the survival of yeast and Lactobacillus during fermentation.

Material and Methods:

Sterile, finely ground corn was mixed with sterile water in a glass fermenter. Next, a commercial enzyme solution containing alpha-amylase and glucoamylase blend (Stargen: Genencor) for processing of uncooked starch was added. Fali Yeast ($10^7$ cfu/g; Fleischmann) used as fermentative yeast was added to the corn slurry mixtures while mixing. Finally, Lactobacillus plantarum (B-4496), obtained from USDA-Microbial Genomics and Bioprocessing Research in Illinois and grown in Difco™ Lactobacilli MRS broth, was used as the representative bacterial contaminant of the fermenter. A formaldehyde based product was added as the final step of the process.

The treatments used are shown in the table below. Samples taken at 4 h, 24 h, 48 h, 72 h and 96 hours were analyzed for Yeast and Lactobacillus counts. The treatments are as follows:

| Treatment | Corn | Water | Enzyme | Yeast ($10^{10}$ cfu/gr) | Lactobacillus ($10^7$ cfu/ml) |
|---|---|---|---|---|---|
| Control | 20 gr | 40 ml | 0.04 ml | 1 gr | 0.02 ml |
| Formula A (1 kg/MT) | 20 gr | 40 ml | 0.04 ml | 1 gr | 0.02 ml |

The results are shown in the following tables:

| | Yeast (cfu/ml) | | | | |
|---|---|---|---|---|---|
| Treatment | 4 h | 24 h | 48 h | 72 h | 96 h |
| Control | $6.8\ 10^8$ | $1.8\ 10^9$ | $2.3\ 10^8$ | $8.0\ 10^8$ | $8.0\ 10^{11}$ |
| Formula A (1 kg/MT) | $7.9\ 10^8$ | $2.3\ 10^9$ | $4.8\ 10^8$ | $8.0\ 10^8$ | $2.0\ 10^9$ |

| | Lactobacillus (cfu/ml) | | | | |
|---|---|---|---|---|---|
| Treatment | 4 h | 24 h | 48 h | 72 h | 96 h |
| Control | $7.6\ 10^5$ | $1.6\ 10^8$ | $1.3\ 10^9$ | $2.9\ 10^{12}$ | $2.2\ 10^8$ |
| Formula A (1 kg/MT) | $6.4\ 10^5$ | $6.8\ 10^7$ | $1.6\ 10^9$ | $1.6\ 10^{12}$ | $9.0\ 10^7$ |

It was observed that 1 kg/ton of the formaldehyde-based product decreased the level of Lactobacillus, but did not affect the level of yeast.

Example 4

The objective of this study was to determine the effect of Formula A on the survival of yeast and Lactobacillus during fermentation.

Material and Methods:

Naturally contaminated whole corn was obtained from a commercial source. The naturally occurring Lactobacillus count in corn was found to be 300 cfu/g. In this study whole corn was treated with Formula A at 0, 1, 2 and 3 kg/MT. After 24 h, 20 g of corn from each treatment was finely ground and added to glass fermenters with water, enzyme and yeast as described below. Samples taken at 4, 24, 48 and 72 hours were analyzed for yeast and Lactobacillus counts. The treatments are as follows:

| Treatment | Corn (gr) | Water (ml) | Enzyme (ml) | Yeast ($10^{10}$ cfu/gr) |
|---|---|---|---|---|
| Control | 20 | 40 | 0.04 | 1 gr |
| Formula A (1 kg/MT) | 20 | 40 | 0.04 | 1 gr |
| Formula A (2 kg/MT) | 20 | 40 | 0.04 | 1 gr |
| Formula A (3 kg/MT) | 20 | 40 | 0.04 | 1 gr |

The results are shown in the following tables:

| | Yeast (cfu/ml) | | | |
|---|---|---|---|---|
| Treatment | 4 h | 24 h | 48 h | 72 h |
| Control | $1.45 \times 10^9$ | $1.0 \times 10^9$ | $1.74 \times 10^9$ | $1.98 \times 10^9$ |
| Formula A (1 kg/MT) | $2.33 \times 10^9$ | $2.0 \times 10^9$ | $1.90 \times 10^9$ | $1.33 \times 10^9$ |
| Formula A (2 kg/MT) | $1.78 \times 10^9$ | $1.8 \times 10^9$ | $1.92 \times 10^9$ | $1.54 \times 10^9$ |
| Formula A (3 kg/MT) | $2.03 \times 10^9$ | $3.3 \times 10^9$ | $1.58 \times 10^9$ | $1.02 \times 10^9$ |

| | Lactobacillus (cfu/ml) | | |
|---|---|---|---|
| Treatment | 24 h | 48 h | 72 h |
| Control | $3.1 \times 10^4$ | $1.2 \times 10^6$ | $1.24 \times 10^7$ |
| Formula A (1 kg/MT) | $1.6 \times 10^3$ | $2.0 \times 10^5$ | $1.0 \times 10^6$ |
| Formula A (2 kg/MT) | $3.0 \times 10^2$ | $1.4 \times 10^4$ | $3.9 \times 10^5$ |
| Formula A (3 kg/MT) | $2.0 \times 10^2$ | 0 | 0 |

It was observed that the use of the formula A did not affect yeast growth and it decreased the number of lactobacillus to 0 at the highest treatment level.

Example 5

The objective of this study was to determine the effect of Formula A on the survival of yeast and Lactobacillus during fermentation.

Material and Methods:

Naturally contaminated whole corn was obtained from a commercial source. The naturally occurring *Lactobacillus* count in corn was found to be 300 cfu/g. In this study, whole corn was treated with Formula A at 0, 1, 2 and 3 kg/MT. After 24 h, 20 g of corn from each treatment was finely ground and added to glass fermenters with water, enzyme and yeast as described below. *Lactobacillus plantarum* (B-4496) grown in MRS broth was added to the fermentation bottles (0.1 ml of $6.2 \times 10^5$ cfu/mL). Samples were taken after 72 hours fermentation for yeast and *Lactobacillus* counts. Treatments are listed on the following table.

| Treatment | Corn (gr) | Water (ml) | Enzyme (ml) | Yeast ($10^{10}$ cfu/gr) | L. plantarum ($6.2 \times 10^5$ cfu/mL) |
|---|---|---|---|---|---|
| Control | 20 | 40 | 0.04 | 1 gr | 0.1 ml |
| Formula A (1 kg/MT) | 20 | 40 | 0.04 | 1 gr | 0.1 ml |
| Formula A (2 kg/MT) | 20 | 40 | 0.04 | 1 gr | 0.1 ml |
| Formula A (3 kg/MT) | 20 | 40 | 0.04 | 1 gr | 0.1 ml |

The results are shown in the following table.

| Treatment | Yeast (cfu/ml) 72 h | Lactobacillus (cfu/ml) 72 h |
|---|---|---|
| Control | $3.7 \times 10^8$ | $1.6 \times 10^7$ |
| Formula A (1 kg/MT) | $2.8 \times 10^8$ | $8.5 \times 10^5$ |
| Formula A (2 kg/MT) | $4.3 \times 10^8$ | $7.5 \times 10^4$ |
| Formula A (3 kg/MT) | $5.7 \times 10^8$ | $5.0 \times 10^3$ |

There was no effect of chemical treatment on yeast concentration. *Lactobacillus* counts decreased as the level of chemical treatment increased in the corn.

Example 6

The objective of this study was to determine the effect of Formula A on the survival of yeast and *Lactobacillus* during fermentation.

Material and Methods:

Naturally contaminated whole corn was obtained from a commercial source. The naturally occurring *Lactobacillus* count in corn was found to be 300 cfu/g. In this study, whole corn was treated with Formula A at 0, 1, 2 and 3 kg/MT. After 24 h., 20 g of corn from each treatment was finely ground and added to glass fermenters with water, enzyme and yeast as described below. *Lactobacillus plantarum* (B-4496) grown in MRS broth was added to the fermentation bottles (0.1 ml of $6.2 \times 10^5$ cfu/mL). Samples were taken after 72 hours fermentation for yeast and *Lactobacillus* counts.

| Treatment | Corn (gr) | Water (ml) | Enzyme (ml) | Yeast ($10^{10}$ cfu/gr) | L. plantarum ($6.2 \times 10^5$ cfu/mL) |
|---|---|---|---|---|---|
| Control | 30 | 100 | 0.15 | 2 gr | 0.2 ml |
| Formula A (1 kg/MT) | 30 | 100 | 0.15 | 2 gr | 0.2 ml |
| Formula A (2 kg/MT) | 30 | 100 | 0.15 | 2 gr | 0.2 ml |
| Formula A (3 kg/MT) | 30 | 100 | 0.15 | 2 gr | 0.2 ml |

The results are shown in the following table.

| Treatment | Yeast (cfu/ml) 72 h | Lactobacillus (cfu/ml) 72 h |
|---|---|---|
| Control | $9.5 \times 10^8$ | $3.5 \times 10^6$ |
| Formula A (1 kg/MT) | $1.25 \times 10^9$ | $7.4 \times 10^4$ |
| Formula A (2 kg/MT) | $7.5 \times 10^8$ | $1.5 \times 10^4$ |
| Formula A (3 kg/MT) | $9.0 \times 10^8$ | $1.7 \times 10^4$ |

There was no effect of chemical treatment on yeast concentration. *Lactobacillus* counts decreased as chemical treatment was increased in the corn.

Example 7

The objective of this study was to determine the effect the formaldehyde on the survival of yeast and *lactobacillus* during fermentation Material and Methods:

Whole corn obtained from a commercial source was treated with formalin (37% formaldehyde solution) at 0, 0.9, 1.8 and 2.7 kg/MT. After 24 h, 30 g of corn from each treatment was finely ground and added to glass fermenters with water, enzyme and yeast as described below. *Lactobacillus plantarum* (B-4496) grown in MRS broth was added to the fermentation bottles (0.2 ml of $6.2 \times 10^5$ cfu/g). Samples were taken after 72 hours fermentation for yeast and *Lactobacillus* counts. The whole content of the fermentations bottles were centrifuged for 30 minutes at 5000 rpm, filtered through cheesecloth and through a 0.45 u tilter to quantify ethanol production. Treatments are listed on the following table

| | Corn (gr) | Water (ml) | Enzyme (ml) | Yeast ($10^{10}$ cfu/gr) | L. plantarum ($6.2 \times 10^5$ cfu/mL) |
|---|---|---|---|---|---|
| Control | 30 | 100 | 0.15 | 2 gr | 0.2 ml |
| Formaldehyde (0.9 kg/MT) | 30 | 100 | 0.15 | 2 gr | 0.2 ml |
| Formaldehyde (1.8 kg/MT) | 30 | 100 | 0.15 | 2 gr | 0.2 ml |
| Formaldehyde (2.7 kg/MT) | 30 | 100 | 0.15 | 2 gr | 0.2 ml |

The results are shown in the following tables.

| Treatment | Yeast (cfu/ml) 72 h | Lactobacillus (cfu/ml) 72 h |
|---|---|---|
| Control | $1.3 \times 10^9$ | 0 |
| Formaldehyde (0.9 kg/MT) | $9.50 \times 10^8$ | 0 |
| Formaldehyde (1.8 kg/MT) | $6.60 \times 10^8$ | 0 |
| Formaldehyde (2.7 kg/MT) | $4.20 \times 10^8$ | 0 |

Conclusions:
1. *Lactobacillus plantarum* inoculum did not multiply in any of the treatments.
2. The use of 37% formaldehyde solution appeared to have a negative effect on yeast growth.

Example 8

The objective of this study was to determine the effect of formaldehyde on the survival of yeast and *Lactobacillus* during fermentation.

Material and Methods:

Whole corn obtained from a commercial source was treated with 37% formaldehyde solution at 0, 0.9, 1.8 and 2.7 kg/MT. After 24 h, 30 g of corn from each treatment was finely ground and added to glass fermenters with water, enzyme and yeast as described below. *Lactobacillus plantarum* (B-4496) grown in MRS broth was added to the fermentation bottles (0.1 ml of $6.2\times10^{10}$ cfu/mL). Samples were taken after 72 hours fermentation for yeast and *Lactobacillus* counts. The whole content of the fermentations bottles were centrifuged for 30 minutes at 5000 rpm, filtered through cheesecloth and through a 0.22 u filter to quantify ethanol production. Treatments are listed on the following table.

| Treatment | Corn (gr) | Water (ml) | Enzyme (ml) | Yeast ($10^{10}$ cfu/gr) | L. plantarum (6.2 × $10^5$ cfu/ml) |
|---|---|---|---|---|---|
| Control | 30 | 100 | 0.15 | 2 gr | 0.2 ml |
| Formaldehyde (0.9 kg/MT) | 30 | 100 | 0.15 | 2 gr | 0.2 ml |
| Formaldehyde (1.8 kg/MT) | 30 | 100 | 0.15 | 2 gr | 0.2 ml |
| Formaldehyde (2.7 kg/MT) | 30 | 100 | 0.15 l | 2 gr | 0.2 ml |

The results are shown in the following tables.

| Treatment | Yeast (cfu/ml) 72 h | *Lactobacillus* (cfu/ml) 72 h |
|---|---|---|
| Control | $1.0 \times 10^9$ | $1.1 \times 10^8$ |
| Formaldehyde (0.9 kg/MT) | $8.8 \times 10^8$ | $9.8 \times 10^7$ |
| Formaldehyde (1.8 kg/MT) | $6.6 \times 10^8$ | $4.7 \times 10^7$ |
| Formaldehyde (2.7 kg/MT) | $8.0 \times 10^8$ | $3.7 \times 10^7$ |

| Density Results | |
|---|---|
| Treatment | Weight of 10 ml Supernatant (gr) |
| Control (water) | 10.0466 |
| Formaldehyde (0.9 kg/MT) | 10.0090 |
| Formaldehyde (1.8 kg/MT) | 10.0183 |
| Formaldehyde (2.7 kg/MT) | 10.0073 |
| Ethanol | 7.9438 |

Conclusions:
1. Formaldehyde produces a slightly decrease (1 log) in cfu's when *Lactobacillus* was added a higher concentrations.
2. Formaldehyde slightly decreased yeast concentration.
3. Formaldehyde treatment decreased the density of fermentation solution indicating an increase in ethanol content.

Examples 9-12

Ethanol production and microbiological profile were analyzed in four fermentation studies using corn treated with 0 (control), 0.45 and 0.90 Kg/MT Formaldehyde. Ground corn and water were mixed and incubated at room temperature in a air-tight 250-ml fermenter jars for 6 hours. This was done in order to increase the naturally occurring *Lactobacillus* in corn. Previous studies have shown that the level of *Lactobacillus* is less than 100 cfu/gr in corn. The other reagents were added into the fermenters as described in the following table.

| Treatment | Corn (gr) | Water (ml) | Enzyme (ml) | Yeast ($10^{10}$ cfu/gr) |
|---|---|---|---|---|
| Control - 0 kg/MT | 30 | 100 | 0.20 | 1.0 gr |
| Formaldehyde - 0.45 kg/MT | 30 | 100 | 0.20 | 1.0 gr |
| Formaldehyde - 0.90 kg/MT | 30 | 100 | 0.20 | 1.0 gr |

After the addition of all the reagents, fermenters were sealed with a cap containing a water trap. Fermenters were kept under constant stirring (low speed) at room temperature (21-23° C.) for 72 hours before sampling for yeast, *Lactobacillus* and alcohol production. *Lactobacillus* counts were determined on MRS broth containing 1.5% Difco™ Agar. Plates were incubated in an anaerobic chamber at 37-C for 48 hours and colonies enumerated. Yeast counts were determined on PDA plates. Plates were incubated at 27° C. for 48 hours and colonies enumerated. Alcohol was determined by FT-IR (FOSS system).

| | Microbiological profile (cfu/gr) after 72-h Fermentation | | | | | | |
|---|---|---|---|---|---|---|---|
| | Study 9 | | Study 10 | | Study 11 | Study 12 | |
| Treatment | Yeast | *Lactobacillus* | Yeast | *Lactobacillus* | Yeast | Yeast | *Lactobacillus* |
| Control | $1.1 \times 10^9$ | $1.1 \times 10^9$ | $7.3 \times 10^8$ | $4.8 \times 10^8$ | $4.7 \times 10^9$ | $2.5 \times 10^9$ | $1.2 \times 10^9$ |
| Formaldehyde 0.45 kg/MT | $9.5 \times 10^8$ | $8.5 \times 10^8$ | $1.2 \times 10^9$ | $5.2 \times 10^8$ | $4.7 \times 10^9$ | $1.8 \times 10^9$ | $8.9 \times 10^8$ |
| Formaldehyde 0.9 kg/MT | $7.4 \times 10^8$ | $7.4 \times 10^8$ | $1.1 \times 10^9$ | $4.3 \times 10^8$ | $3.6 \times 10^9$ | $1.8 \times 10^9$ | $9.4 \times 10^8$ |

| Ethanol Concentration (%) in Fermented Liquid | | | |
|---|---|---|---|
| | Formaldehyde Treatment | | |
| Study | control | 0.45 kg/Mt | 0.90 kg/Mt |
| 9 | 9.3 | 9.7 | 10.3 |
| 10 | 9.6 | 9.4 | 9.6 |
| 11 | 8.9 | 9.1 | 9.2 |
| 12 | 8.3 | 8.6 | 8.3 |
| AVG | 9.025 | 9.2 | 9.35 |
| % increase | | 2% | 3.60% |

From these studies we can concluded that the treatment of corn with formaldehyde improved ethanol yield. This effect appears to be due to the control of *Lactobacillus*.

Examples 13-16

Wild *Lactobacillus* and yeast/mold profile were determined in four studies using corn treated with 0 (control), 0.45 and 0.90 Kg/MT Formaldehyde (HCHO). Ground corn and water were mixed and incubated at room temperature (21-23° C.) in an anaerobic environment for 24 hours. To 5 gr of ground corn 45 ml of Butterfield was added and incubated overnight in a closed container while stirring at room temperature. After incubation, samples were taken to enumerate wild yeast/mold and *Lactobacillus*. Results are presented in the following table.

| | Microbiological Profile (cfu/gr) after 24-h Incubation | | | | | | | |
|---|---|---|---|---|---|---|---|---|
| | Study 1 | | Study 2 | | Study 3 | | Study 4 | |
| Treatments | Yeast | Lactobacillus | Yeast | Lactobacillus | Yeast | Lactobacillus | Yeast | Lactobacillus |
| Control | $1.0 \times 10^6$ | $2.0 \times 10^6$ | $1.3 \times 10^7$ | $5.0 \times 10^7$ | $1.7 \times 10^5$ | $2.5 \times 10^6$ | $8.6 \times 10^5$ | $1.8 \times 10^7$ |
| Formaldehyde 0.45 kg/MT | $3.0 \times 10^5$ | $4.0 \times 10^5$ | $7.0 \times 10^5$ | $9.3 \times 10^5$ | $1.6 \times 10^5$ | $2.9 \times 10^4$ | $3.2 \times 10^5$ | $7.7 \times 10^5$ |
| Formaldehyde 0.9 kg/MT | $7.6 \times 10^4$ | $6.2 \times 10^4$ | $5.6 \times 10^6$ | $1.2 \times 10^4$ | $2.0 \times 10^3$ | $9.0 \times 10^3$ | $2.6 \times 10^5$ | $8.1 \times 10^4$ |

These studies showed a reduction in *Lactobacillus* and yeast/mold levels on corn treated with formaldehyde.

It will be apparent to those skilled in the art that variations and modifications of the invention can be made without departing from the sprit and scope of the teachings above. It is intended that the specification and examples be considered as exemplary only and are not restrictive.

The invention claimed is:

1. A high yield method of fermenting polysaccharides to ethanol, comprising:
   a) treating a polysaccharide to be fermented with a composition containing formaldehyde,
   1-50 wt. % of a surfactant having an HLB from 4 to 18,
   0-20 wt. % of an antimicrobial terpene, or essential oils,
   1-50 wt. % of organic acids selected from $C_1$ to $C_{24}$ fatty acids, their salts, glycerides and esters thereof, and
   1-50 wt. % water to produce a treated polysaccharide;
   b) fermenting said treated polysaccharide in a fermentation broth containing yeast,
   38-333 ppm formaldehyde, and hydrolytic enzymes effective to hydrolyze said treated polysaccharide to simple sugars; and
   c) isolating ethanol.

2. The fermentation method of claim 1, wherein the organic acid, is formic, acetic, propionic, or butyric.

3. The fermentation method of claim 1, comprising an antibiotic to control lactobacillus in an amount less than its MIC in fermentations without composition a).

4. The fermentation method of claim 1, which is free of antibiotic used to control bacteria in fermentation.

5. The fermentation method of claim 1, which is free of virginiamycin.

6. The fermentation method of claim 1, wherein material remaining after fermentation is collected and added to animal feed.

7. The method of claim 1, wherein the polysaccharide to be fermented is obtained from corn, sorghum, wheat, triticale, rye:, barley, rice or tubers.

8. The method of claim 1, wherein the polysacchlaride to be fermented is cellulose.

9. The method of claim 1, wherein ethanol coproducts remaining after fermentation are collected and used as animal feed or food.

* * * * *

UNITED STATES PATENT AND TRADEMARK OFFICE
CERTIFICATE OF CORRECTION

PATENT NO. : 8,883,470 B2  
APPLICATION NO. : 13/388664  
DATED : November 11, 2014  
INVENTOR(S) : Pimentel et al.

Page 1 of 1

It is certified that error appears in the above-identified patent and that said Letters Patent is hereby corrected as shown below:

In the Claims

Column 16 line 15 change: "acid, is formic, acetic, propionic, or butyric." to -- acid is formic, acetic, propionic, or butyric. --

Column 16 line 18 change: "MIC in fermentations without composition a)." to -- MIC in fermentations without composition. --

Column 16 line 28 change: "rye:, barley, rice or tubers." to -- rye, barley, rice or tubers. --

Column 16 line 29 change: "8. The method of claim 1, wherein the polysacchlaride to" to -- 8. The method of claim 1, wherein the polysaccharide to --

Signed and Sealed this  
Twenty-fourth Day of February, 2015

Michelle K. Lee  
*Deputy Director of the United States Patent and Trademark Office*